United States Patent [19]

Liebowitz

[11] Patent Number: 4,781,919
[45] Date of Patent: * Nov. 1, 1988

[54] SUSTAINED RELEASE DOSAGE FORM

[75] Inventor: Stephen M. Liebowitz, Somerville, N.J.

[73] Assignee: Schering Corporation, Kenilworth, N.J.

[*] Notice: The portion of the term of this patent subsequent to Dec. 15, 2004 has been disclaimed.

[21] Appl. No.: 132,530

[22] Filed: Nov. 14, 1987

Related U.S. Application Data

[63] Continuation-in-part of Ser. No. 621,580, Jun. 18, 1984, Pat. No. 4,713,237.

[51] Int. Cl.$^4$ ............................................. A61K 31/78
[52] U.S. Cl. ........................................ 424/78; 424/81; 424/422
[58] Field of Search ........................... 424/78, 81, 422

[56] References Cited

U.S. PATENT DOCUMENTS 4,713,237 12/1987 Shah ...................................... 424/78

Primary Examiner—Shep K. Rose
Attorney, Agent, or Firm—Richard C. Billups; James R. Nelson; Stephen I. Miller

[57] ABSTRACT

Sustained release dosage forms are made of saponified starch-acrylonitrile graft copolymers and an active ingredient.

3 Claims, No Drawings

SUSTAINED RELEASE DOSAGE FORM

CROSS REFERENCE TO RELATED APPLICATION

This application is a continuation-in-part of U.S. application Ser. No. 621,580 filed on June 18, 1984 now U.S. Pat. No. 4,713,237 and copending herewith, priority of which is claimed hereunder.

This invention relates to a sustained release dosage form capable of slowly releasing an active ingredient therefrom.

Numerous prior publications disclose various polymers for slowly releasing active ingredients. See for example Schor et al, U.S. Pat. No. 4,369,172 (hydroxypropylmethyl cellulose); Hasler et al, U.S. Pat. No. 4,105,823 (starches, polyanhydrides, polyacrylamide and acrylates); Dannelly, U.S. Pat. No. 4,177,255 (cellulose esters, polyvinylchloride, polystyrene, polymethyl methacrylate, etc); Shepherd et al, U.S. Pat. No. 3,577,512 (hydrophilic acrylates); Takeabe et al, U.S. Pat. No. 3,919,436 (substituted acrylamide); Merabi et al, U.S. Pat. No. 3,495,000 (dialdehyde starch mixed with other ingriedients); and Anderson et al, U.S. Pat. No. 3,909,444 (various synthetic polymers and cellulose derivative).

The present invention concerns use of saponified starch-acrylonitrile graft copolymers for sustained release of active ingredients. These particular copolymers have not previously been used for this purpose. These graft copolymers are known to be water swellable, but not water soluble. Surprisingly it has been found that saponified starch-acrylonitrile graft copolymers provide highly desirable sustained release of the active ingredient.

SUMMARY OF THE INVENTION

The present invention comprises a sustained release dosage form comprising an active ingredient and saponified starch-acrylonitrile graft copolymer.

DETAILED DESCRIPTION OF THE INVENTION

Saponified starch-acrylonitrile graft copolymers are manufactured by preparing a graft copolymer of starch and acrylonitrile with starch as the backbone and acrylonitrile as the branches. The copolymer is then saponified in a solution of alkali metal hydroxide to form a copolymer having a structure equivalent to a starch-acrylamide-alkali metal acrylate graft copolymer wherein starch is the backbone and acrylamide and alkali metal acrylate form the branches. This manufacturing process is described in U.S. Pat. Nos. 3,661,815, 4,116,899, and a product brochure entitled SGP ABSORBENT POLYMER published by Henkel Corporation, incorporated by reference. The graft copolymer may be blended with fatty quaternary ammonium chloride as described in U.S. Pat. No. 4,159,260, incorporated by reference.

Suitable saponified starch-acrylonitrile graft copolymers are sold under the tradenames SGP by Henkel Corporation, Minneapolis, MN. and WATERLOCK by Grain Processing Corporation, Muscatine, Iowa. These products are known for their ability to absorb large quantities of water, but their use in slow release dosage forms is believed novel.

One saponified starch polyacrylonitrile copolymer used herein has the structural formula:

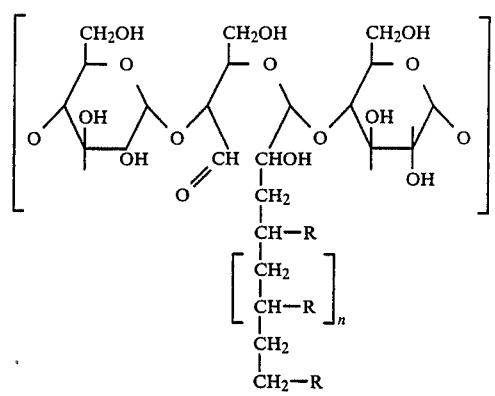

wherein R is $—CONH_2$ or $CO_2Na$.

Other saponified starch polyacrylonitrile copolymers may be used as well.

To make sustained release dosage forms in accordance with the invention, the saponified starch-acrylonitrile graft copolymers are blended with the active ingriedient and then formed into the desired dosage form by methods well known to those skilled in the art. Examples of dosage forms include capsules, oral liquids, tablets, implants, topical lotions, creams or ointments, opthalmic gels, vaccines, injectable solutions and suspensions, suppositories, etc. Active ingredients may be any desirable substance or combination of substances such as aspirin, salicylic acid, sodium salicylate, APAP, steroids, antibiotics, pilocarpine, pseudophedrine base, pseudophedrine sulfate, chloramphenical, antibiotics, polypeptides, growth promoter, anthelmintics, etc.

To make sustained dosage forms in accordance with the invention, saponified starch-acrylonitrile graft copolymer is mixed with the active ingredient and the mixture is then placed into the desired form. For example, to form a tablet, compass the mixture in a conventional tablet press. To form a suspension for injection or oral administration, mix the mixture with appropriate liquids.

EXAMPLES

The following examples illustrate the effect of saponified starch-acrylonitrile graft copolymer on the show release of various active ingredients. Two graft copolymers were used: (1) SGP 502S, manufactured by Henkel Corporation, and (2) SGP 104, which is made by blending SGP 502S with a fatty quaternary ammonium chloride.

For all examples, tablets were made by compressing 250 mg of a mixture of active ingredient and graft copolymer at 4000 lb pressure on a Carver Tablet press using 11/36" standard concave punches.

To test the release properties of the tablet, simulated gastric fluid (SGF) and simulated intestinal fluid (SIF) were prepared according to USP XX. The dissolution rates of the active ingredients were determined at various times at 37° C.

EXAMPLES WITH SALICYLIC ACID AS THE ACTIVE INGREDIENT

| Example No. | | 1 | 2 | 3 | 4 |
|---|---|---|---|---|---|
| Wt. % SGP 104 | | 0 | 30 | 50 | 70 |
| Wt. % Salicylic Acid | | 100 | 70 | 50 | 30 |
| Time, Hrs | Fluid | % Salicylic Acid Dissolved | | | |
| 1 | SGF | 13 | 48 | 12 | 14 |
| 2 | SIF | 45 | 87 | 21 | 30 |
| 3 | SIF | 68 | | 32 | 49 |
| 4 | SIF | 83 | | 44 | 69 |
| 5 | SIF | 97 | | 57 | 82 |
| 6 | SIF | | | 65 | 90 |
| 18 | SIF | | | 103 | 101 |

The above examples show how the dissolution rate of salicylic acid can be varied with varying concentrations of the graft copolymer.

| Example No. | | 5 | 6 | 7 | 8 |
|---|---|---|---|---|---|
| Wt. % SGP 502S | | 0 | 30 | 50 | 70 |
| Wt. % Salicylic Acid | | 100 | 70 | 50 | 30 |
| Time, Hrs | Fluid | % Salicylic Acid Dissolved | | | |
| 1 | SGF | 13 | 8 | 10 | 18 |
| 2 | SIF | 45 | 18 | 23 | 39 |
| 3 | SIF | 68 | 28 | 40 | 65 |
| 4 | SIF | 83 | 37 | 56 | 80 |
| 5 | SIF | 97 | 43 | 65 | 103 |
| 6 | SIF | | 49 | 72 | |
| 24 | SIF | | 102 | 100 | |

EXAMPLES WITH SODIUM SALICYLATE AS THE ACTIVE INGREDIENT

| Example No. | | 9 | 10 | 11 | 12 |
|---|---|---|---|---|---|
| Wt. % SGP 104 | | 0 | 30 | 50 | 70 |
| Wt. % Sodium Salicylate | | 100 | 70 | 50 | 30 |
| Time, Hrs | Fluid | % Sodium Salicylate Dissolved | | | |
| 1 | SGF | 100 | 102 | 28 | 24 |
| 2 | SIF | | | 57 | 47 |
| 3 | SIF | | | 77 | 67 |
| 4 | SIF | | | 84 | 78 |
| 5 | SIF | | | 89 | 86 |

| Example No. | | 13 | 14 | 15 | 16 |
|---|---|---|---|---|---|
| Wt. % SGP 502S | | 0 | 30 | 50 | 70 |
| Wt. % Sodium Salicylate | | 100 | 70 | 50 | 30 |
| Time, Hrs | Fluid | % Sodium Salicylate Dissolved | | | |
| 1 | SGF | 100 | 102 | 32 | 28 |
| 2 | SIF | | | 71 | 63 |
| 3 | SIF | | | 84 | 79 |
| 4 | SIF | | | 92 | 89 |
| 5 | SIF | | | 95 | 94 |

Examples 9 through 16 show how a very rapidly dissolving active ingredient can be slowly released using the present invention.

EXAMPLES WITH PSEUDOEPHEDRINE BASE (PB) AS THE ACTIVE INGREDIENT

| Example No. | | 17 | 18 | 19 | 20 | 21 |
|---|---|---|---|---|---|---|
| Wt. % SGP 104 | | 0 | 30 | 50 | 60 | 70 |
| Wt. % PB | | 100 | 70 | 50 | 40 | 30 |
| Time, Hrs | Fluid | % PB Dissolved | | | | |
| 1 | SGF | 100 | 63 | 25 | 21 | 24 |
| 2 | SIF | | 100 | 62 | 30 | 32 |
| 3 | SIF | | | 87 | 45 | 43 |
| 4 | SIF | | | 95 | 57 | 64 |
| 5 | SIF | | | | 70 | 78 |
| 6 | SIF | | | | 83 | 93 |
| 7 | SIF | | | | 89 | |

| Example No. | | 22 | 23 | 24 | 25 | 26 |
|---|---|---|---|---|---|---|
| Wt. % SGP 502S | | 0 | 30 | 50 | 60 | 70 |
| Wt. % PB | | 100 | 70 | 50 | 40 | 30 |
| Time, Hrs | Fluid | % PB Dissolved | | | | |
| 1 | SGF | 100 | 64 | 25 | 21 | 22 |
| 2 | SIF | | 95 | 66 | 30 | 28 |
| 3 | SIF | | | 90 | 45 | 34 |
| 4 | SIF | | | 96 | 57 | 40 |
| 5 | SIF | | | | 70 | 58 |
| 6 | SIF | | | | 83 | 59 |
| 7 | SIF | | | | 89 | |

Example 17 to 26 also illustrate the sustained release of a rapidly dissolving ingredient.

EXAMPLES WITH PSEUDOEPHEDRINE SULFATE (PS) AS THE ACTIVE INGREDIENT

| Example No. | | 27 | 28 | 29 | 30 | 31 |
|---|---|---|---|---|---|---|
| Wt. % SGP 104 | | 0 | 30 | 40 | 50 | 70 |
| Wt. % PS | | 100 | 70 | 60 | 50 | 30 |
| Time, Hrs | Fluid | % PS Dissolved | | | | |
| 1 | SGF | 100 | 94 | 45 | 39 | 33 |
| 2 | SIF | | | 63 | 52 | 40 |
| 3 | SIF | | | 69 | 59 | 45 |
| 4 | SIF | | | 79 | 66 | 52 |
| 5 | SIF | | | 82 | 69 | 58 |
| 6 | SIF | | | 87 | 76 | 65 |
| 7 | SIF | | | 89 | | |

| Example No. | | 32 | 33 | 34 | 35 | 36 |
|---|---|---|---|---|---|---|
| Wt. % SGP 502S | | 0 | 30 | 40 | 50 | 70 |
| Wt. % PS | | 100 | 70 | 60 | 50 | 30 |
| Time, Hrs | Fluid | % PS Dissolved | | | | |
| 1 | SGF | 100 | 56 | 30 | 24 | 25 |
| 2 | SIF | | 76 | 41 | 33 | 32 |
| 3 | SIF | | 87 | 47 | 38 | 38 |
| 4 | SIF | | | 52 | 44 | 45 |
| 5 | SIF | | | 59 | 48 | 46 |
| 6 | SIF | | | 62 | 52 | 51 |
| 7 | SIF | | | 67 | 57 | 55 |

EXAMPLES WITH CHLORAMPHENICOL (C) AS THE ACTIVE INGREDIENT

| Example No. | | 37 | 38 | 39 | 40 |
|---|---|---|---|---|---|
| Wt. % SGP 104 | | 0 | 30 | 50 | 70 |
| Wt. % C | | 100 | 70 | 50 | 30 |
| Time, Hrs | Fluid | % C Dissolved | | | |
| 1 | SGF | 5 | 67 | 37 | 14 |
| 2 | SIF | 26 | 92 | 87 | 50 |
| 3 | SIF | 42 | | 61 | |
| 4 | SIF | 53 | | 93 | |
| 5 | SIF | 62 | | 104 | |
| 6 | SIF | 70 | | | |
| 7 | SIF | 75 | | | |

In Examples 38 to 40, the graft copolymers increased the rate of dissolution of the active ingredient, which could be advantageous in many cases.

| Example No. | | 41 | 42 | 43 | 44 | 45 |
|---|---|---|---|---|---|---|
| Wt. % SGP 502S | | 0 | 30 | 50 | 60 | 70 |
| Wt. % C | | 100 | 70 | 50 | 40 | 30 |
| Time, Hrs | Fluid | | | % C Dissolved | | |
| 1 | SGF | 5 | 85 | 12 | 13 | 9 |
| 2 | SIF | 26 | 91 | 77 | 51 | 14 |
| 3 | SIF | 42 | | 86 | 74 | 19 |
| 4 | SIF | 53 | | 95 | 91 | 24 |
| 5 | SIF | 62 | | | 97 | 30 |
| 6 | SIF | 70 | | | 100 | 35 |
| 7 | SIF | 75 | | | | — |
| 24 | SIF | | | | | 103 |

The following are examples of parenteral formulations which utilize a saponified co-polymer in combination with an active ingredient to provide sustained release thereof. The parenteral formulation ideally encompasses a combination of a saponified copolymer and at least one active ingredient in a nonaqueous vehicle. The polymer hydrates over a period of time after the preparation is injected into a mammal in need of sustained release of the active ingredient contained therein. Upon hydrating, the polymer causes sustained release of the active compound over an extended period of time.

Suitable solvents for the sustained release formulation in injectable form include, for example, propylene glycol, polyethylene glycol 200, polyethylene glycol 400, ethanol, N-methyl-2-pyrrolidone, or a combination of the above, such that the water content contained therein is generally less than about five percent. Of course use of certain solvents, such as ethanol, are limited in that they may cause unnecessary discomfort upon injection, and should therefore be limited to less than about 10 percent of the total volume of the injection. In example 46 below, the solvent system is comprised of the solvents described above.

EXAMPLE 46

| | % weight |
|---|---|
| Salicylic acid | 26–70 |
| Polymer SGP 502S | 70–26 |
| Tween 20 | 0.5–1.0 |
| Tween 80 | 1.0–2.5 |
| Methocel A4C | 0.15–0.20 |
| Solvent system | qs ad 100% |

PROCEDURE

Mix the drug and polymer intimately and subject the mixture to dry compression or dry granulation. Mill the resulting slugs or granulation to the desired mesh size suitable to prepare a pharmaceutically acceptable suspension, useful for intramuscular or subcutaneous injection. Take up the suspension in the solvent system as described above, and package in 10 ml or single use vials.

While Applicant has described what are believed to be certain preferred embodiments of the invention, other alternative embodiments not specifically described fall within the scope of the invention as described and claimed. Consequently the scope of the invention is not to be limited thereby.

I claim:

1. A sustained release injectable dosage form comprising an effective amount of an active ingredient, and an effective amount of a water insoluble, water swellable, saponified starch acrylonitrile graft copolymer to provide sustained release of said active ingredient upon injection into a patient in need of such treatment.

2. A sustained release dosage form as in claim 1 wherein the saponified starch-acrylonitrile graft copolymer is

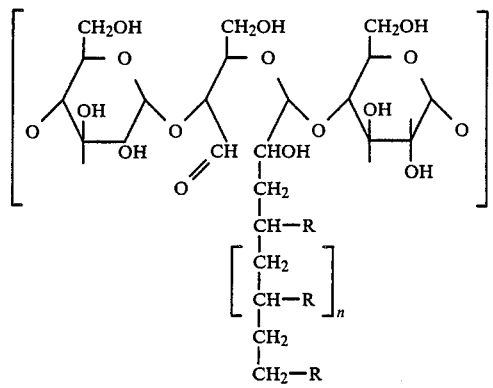

$R = CONH_2$ or $-CO_2Na$.

3. A sustained release dosage form as defined in claim 1 wherein the dosage form is a suspension.

* * * * *